Figure 1:
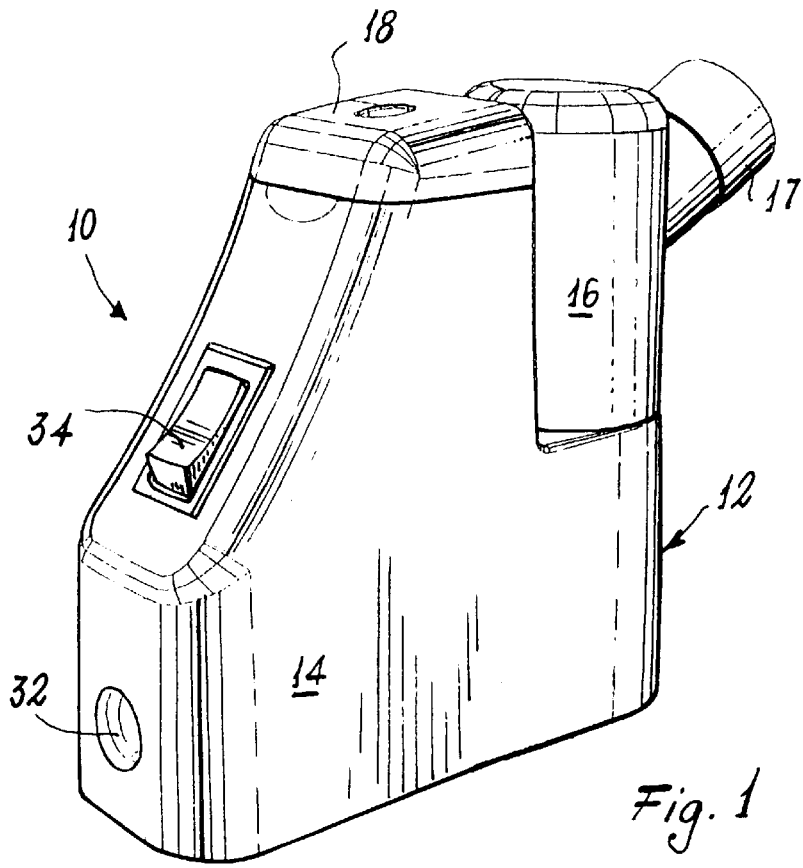

United States Patent
Fraccaroli

Patent Number: 5,803,362
Date of Patent: Sep. 8, 1998

[54] ULTRASONIC AEROSOL APPARATUS

[75] Inventor: Nicola Fraccaroli, Brescia, Italy

[73] Assignees: Miat S.p.A., Milan; MED 2000 Srl, Brescia, both of Italy

[21] Appl. No.: 634,270

[22] Filed: Apr. 18, 1996

[30] Foreign Application Priority Data

Aug. 3, 1995 [IT] Italy .................................. MI95A1717

[51] Int. Cl.⁶ .................................................. B05B 17/06
[52] U.S. Cl. ........................ 239/102.2; 239/338; 310/315
[58] Field of Search ................. 239/102.2, 338, 239/63, 4; 310/315, 341, 323, 325

[56] References Cited

U.S. PATENT DOCUMENTS

| | | | |
|---|---|---|---|
| 3,839,651 | 10/1974 | Michaels | 307/308 |
| 4,001,650 | 1/1977 | Romain | 317/41 |
| 4,400,705 | 8/1983 | Horike | 310/315 X |
| 4,641,053 | 2/1987 | Takeda | 239/102.2 |
| 4,660,057 | 4/1987 | Watanabe et al. | 310/315 X |
| 4,732,322 | 3/1988 | Gaysert et al. | 239/102.2 |
| 4,767,960 | 8/1988 | Strobel | 310/338 |
| 4,834,124 | 5/1989 | Honda | 239/102.2 X |
| 4,877,989 | 10/1989 | Drews et al. | 239/102.2 X |
| 5,145,113 | 9/1992 | Burwell et al. | 310/323 X |
| 5,145,323 | 9/1992 | Farr | 417/36 |
| 5,624,608 | 4/1997 | Ching et al. | 239/102.2 X |

Primary Examiner—Kevin Weldon
Attorney, Agent, or Firm—Ladas & Parry

[57] ABSTRACT

An ultrasonic aerosol apparatus having a piezoelectric element which generates ultrasonic signals in response to signals received from an oscillating circuit, where the temperature of the piezoelectric element is controlled by an electronic device such as an N.T.C. thermistor. The temperature control device senses the temperature of the piezoelectric element and controls the power fed to the oscillator circuit in accordance with the temperature of the piezoelectric element. Rather than cut power completely to the oscillator circuit (thereby interrupting the atomization process of the apparatus), the temperature control device reduces power fed to the oscillator circuit when the piezoelectric element temperature rises above a predetermined value, and increases power fed to the oscillator circuit when the piezoelectric element temperature falls below a predetermined value. Leakage of liquids (e.g., water or medication) contained within the apparatus is avoided by the lack of joints in the liquid-holding apparatus containers. The piezoelectric element may be ceramic, and may be supported by an elastic element which itself may act as an electrical connection between the piezoelectric element and the temperature control device.

17 Claims, 2 Drawing Sheets

ULTRASONIC AEROSOL APPARATUS

This invention relates to an aerosol apparatus of ultrasonic type.

As is well known to the expert of the art, known ultrasonic aerosol apparatus are provided with a protection thermostat to prevent overheating of the ceramic piezoelectric element which emits the ultrasound.

These thermostats are in the usual form of self-resetting thermal switches. In this specific case, when the ceramic piezoelectric element overheats to beyond a preset temperature, the thermostat operates to interrupt power to the relative oscillator. When the temperature of the ceramic element again falls below the preset temperature the thermostat restores the electrical connection, so that the entire power of the oscillator is fed to the ceramic element.

This type of automatic control for preventing ceramic element overheating has a first drawback due to the fact that the piezoelectric ceramic element is subjected to sudden thermal stresses which in the long term compromise its operation. A second drawback is the cessation of atomization when the thermostat operates.

Figure 2:
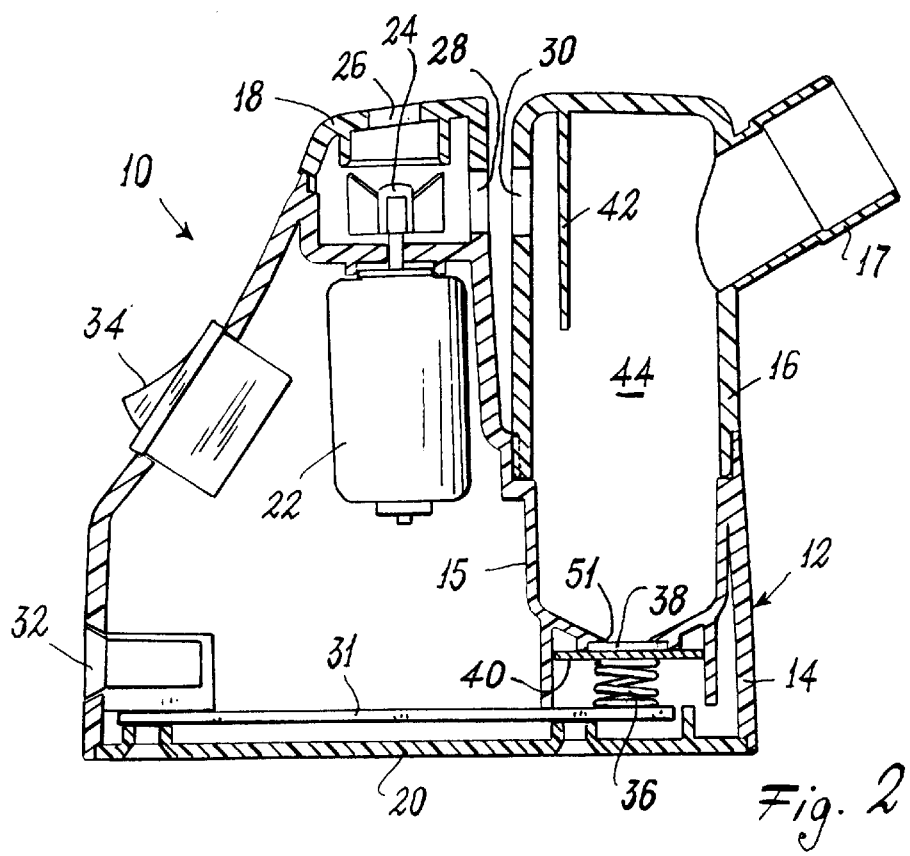

It is also well known to the expert of the art that conventional ultrasonic aerosol apparatus are basically of two types. A first type is known as the indirect atomization type in the sense that between the piezoelectric ceramic element and the liquid medicament to be atomized there is interposed a suitable mass of water (from half a cup to half a litre of tap water), to be previously poured by the patient into a relative container provided in the apparatus. In the water of this container there is immersed a second container into which the liquid medicament to be atomization is poured.

In some of these aerosol apparatus of indirect atomization type, because of the fact that the patient may not have poured a sufficient water quantity into the first container or because the apparatus may not be held vertically during use (it has been found that the patient often tends to incline the apparatus), a second drawback can arise due to the fact that the tip of the ultrasound generated by the piezoelectric ceramic element does not fall into the medicament contained in the second container but instead falls below it. The result is that the water in the first container is atomized. As some of these apparatus are provided with a ventilation device which causes an air stream to flow over the free surface of the water contained in the first container, the patient breathes in tap water, which is absolutely contraindicated for an asthmatic.

To avoid this second drawback, aerosol apparatus of direct atomization type have been constructed in which the mass of water interposed between the piezoelectric ceramic element has been eliminated. However to protect the piezoelectric ceramic element from thermal expansion an aluminium screen has to be glued to it. This screen is circular and on it there is glued a stainless steel protection disc, the purpose of which is to protect the aluminium disc from chemical attack by the medicament. This double protection for the piezoelectric ceramic element not only reduces the ultrasound power transmitted by it but also considerably affects the manufacturing cost of the aerosol apparatus. In addition the adhesive bonding of the various discs can be damaged with use, as ultrasound is devastating from this viewpoint.

A third drawback of known ultrasonic aerosol apparatus is that the apparatus casing, of plastics construction, is formed in two substantially identical halves joined together by snap-engagement means or by screws. The joint between these two halves involves the first and/or the second said containers and does not ensure a perfect seal, or at least not in the long term, so that the liquid medicament and/or water can leak to reach the electrical or electronic part of the apparatus, with the obvious drawbacks deriving therefrom.

A fourth drawback of conventional ultrasonic aerosol apparatus is the fact that the piezoelectric ceramic element rests on conductive metal rings electrically connected directly or via wires to the printed circuit. This arrangement can result in a variation in the ceramic vibration frequency, with obvious problems arising.

An object of the present invention is to obviate the first aforesaid drawback. This object is attained by the apparatus of the present invention, characterised in that the temperature of the piezoelectric ceramic element is controlled by a control circuit comprising an electronic component or device of negative temperature coefficient impedance (N.T.C.), for example of the type known to the electronics expert as an N.T.C. thermistor. A further object is to obviate the second aforesaid drawback, this being attained by the aerosol apparatus of the present invention, of either the direct or indirect atomization type, wherein the piezoelectric ceramic element is of the vitrified and/or teflon-coated type.

A further object is to overcome the third aforesaid drawback, this object being attained by the aerosol apparatus of the present invention, in which the joints between the component parts of the apparatus casing do not involve either the water container if the apparatus is of indirect atomization type, or the container for the liquid medicament to be atomized.

A further object of the invention is to obviate the fourth aforestated drawback, this object being attained by the aerosol apparatus of the present invention, wherein the piezoelectric ceramic element is supported by elastic means. In particular these elastic means are of an electrically conductive material and also act as the electrical connection between the piezoelectric ceramic element and the N.T.C. thermistor.

The invention will be more apparent from the following description of one embodiment thereof. In this description reference is made to the accompanying drawings, in which:

FIG. 1 is an isometric view of the aerosol apparatus according to the present invention;

FIG. 2 is a vertical section therethrough on its central plane, showing the various components of the aerosol apparatus enclosed in the relative casing;

FIG. 3 is a possible electrical schematic of the apparatus according to the present invention.

As can be seen from FIGS. 1 and 2, the aerosol apparatus 10 has a casing 12 enclosing the various components of the apparatus. The casing 12 consists of four parts, namely a first larger-dimension part 14 comprising nearly the entire lateral surface of the casing 12, a second part 16 provided with a nozzle 17, a third part 18 enclosing a fan 24, and a fourth lower closure part 20. The first part 14 comprises a cup element 15.

The parts 14, 16, 18 and 20 are conveniently constructed of a suitable plastics material and are joined together by means of an interference fit or by pressure, with the exception of the fourth part which in this specific case is maintained in position by screws (not shown). These four parts forming the casing 12 are therefore mutually separable.

The first part 14 of the casing 12 encloses and supports an electric motor 22 for operating the fan 24, which is enclosed within the third part 18 and draws air through an upper aperture 26 to expel it through a lateral aperture 28 facing an aperture 30 provided in the second part 16.

The first part 14 internally supports a printed circuit card 31 connected via a switch 34 to a usual current socket 32 connectable to the electricity mains by an electric cable (not shown) via a transformer. Two concentric helical metal springs both indicated by 36 (of which the outer one is visible in FIG. 2) are fixed onto the card 31. Besides elastically supporting a piezoelectric ceramic disc 38, these springs also provide electrical connection between the printed circuit 31 and the electrical contacts (not visible) provided on the ceramic element. The cup 15 comprises in its base a hole 51 lowerly closed by the piezoelectric ceramic element 38. The electric motor 22 is powered via the socket 32 and the switch 34.

Figure 3:
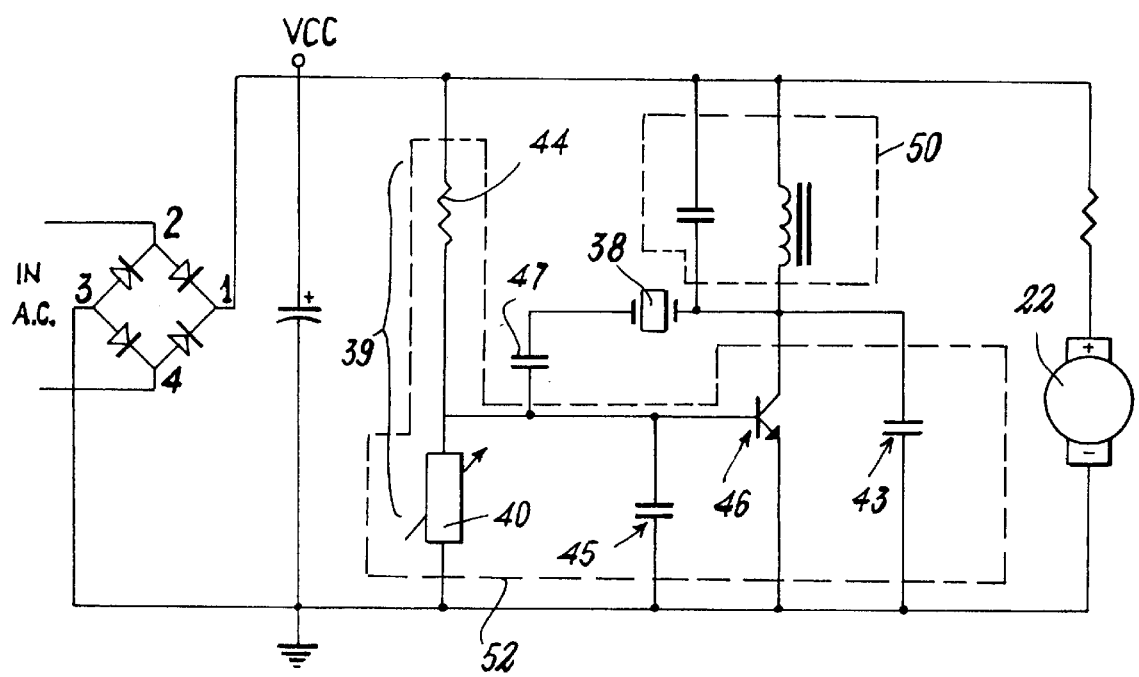

As already stated, FIG. 3 shows a possible electrical schematic or circuit for the aerosol apparatus 10, comprising an ultrasound generator with an oscillator circuit 50 and a piezoelectric ceramic element 38, and means 52 for protecting the ceramic element from excess temperature. The protection means 52 comprise an N.T.C. thermistor 40, i.e. an electronic component or device of negative temperature coefficient impedance. The N.T.C. thermistor 40 together with a resistor 44 form a voltage divider 39, the voltage drop across the N.T.C. thermistor being applied to a transistor 46 in series with the oscillating circuit 50. A first capacitor 45 is connected in parallel with the N.T.C. thermistor 40. A second capacitor 43 is connected in parallel with the transistor 46 and a third capacitor 47 is connected in series with the ceramic element 38.

The schematic of FIG. 3 is not described in detail herein, inasmuch as the circuit schematic of FIG. 3 can be readily understood by a person of ordinary skill in the art. However, it should however be noted that as the N.T.C. thermistor is positioned in direct contact with or at least in proximity to the ceramic element, when the temperature of this latter begins to rise the potential across the N.T.C. thermistor 40 and hence at the base of the transistor 46 is reduced, with consequent gradual reduction of the power fed to the oscillating circuit 50. In contrast, as the temperature decreases, the power fed to said circuit is gradually increased.

Because of the N.T.C. thermistor, the piezoelectric ceramic element 38 is no longer subjected to sudden thermal stressing as in the case of known apparatus, and in addition there are no longer sudden interruptions in atomization.

A brief description will now be given of the use and operation of the aforedescribed apparatus 10.

By removing the second part 16 of the casing 12 the liquid medicament to be atomized can be fed into the cup 15 to collect on the cup bottom above the piezoelectric ceramic element 38. On replacing the part 16 and operating the switch 34, two effects are obtained, namely the piezoelectric ceramic element 38 generates ultrasound to atomize the liquid medicament contained in the cup 15, and the fan 24 is operated by which an air stream leaves the aperture 28 to pass through the aperture 30 and then descend by virtue of the baffle 42 provided in the second part 16. During the operation of the switch 34, the patient draws through the nozzle 17, by which action the air stream leaving the aperture 28 is drawn through the aperture 30 to remove the atomized medicament from the chamber 44 and enable it to be drawn in by the patient. The medicament atomization effect and the action of the fan 24 cease when the patient again presses the switch 34.

As is apparent to the expert of the art, the aforedescribed apparatus 10 is of the direct atomization type. It will however also be apparent to the expert of the art that an ultrasonic aerosol apparatus of indirect atomization can be formed embodying the characteristics of the present invention.

I claim:
1. An ultrasonic aerosol apparatus, comprising an ultrasound generator with an oscillator circuit (50), a piezoelectric ceramic element (38), and means (52) for protecting the ceramic element from excess temperature, said means (52) comprising an electronic device (40) responsive to the temperature of the ceramic element, the device reducing power fed to the oscillator circuit (50) when the temperature of the ceramic element rises over a predetermined value and increasing power fed to the oscillator circuit (50) when the temperature of the ceramic element falls below said value, the device forming part of a voltage divider (39) wherein a voltage drop exists across the device (40), the voltage drop across the device (40) being applied to a transistor (46) in series with the oscillator circuit (50).

2. An apparatus as claimed in claim 1, wherein the electronic device is a negative temperature coefficient thermistor (40).

3. An apparatus as claimed in claim 1, wherein a capacitor (43) is connected in parallel with the transistor (46).

4. An apparatus as claimed in claim 1, wherein a capacitor (45) is connected in parallel with the electronic device (40).

5. An apparatus as claimed in claim 1, wherein the ceramic element (38) has an electrode, the electrode being connected via a capacitor (47) to a transistor (46).

6. An apparatus as claimed in claim 1, wherein further comprises an apparatus casing having component parts assembled together to define joints between the component parts, and at least one container carrying a liquid.

7. An apparatus as claimed in claim 1, wherein the apparatus further comprises a printed circuit card (31) containing a printed circuit, and wherein the piezoelectric ceramic element is supported by elastic means, the elastic means being an electrically conductive material and acting as an electrical connection between the piezoelectric ceramic element and the printed circuit on the printed circuit card (31).

8. An ultra-sonic aerosol apparatus comprising:
   an oscillator circuit;
   a transistor connected in series with the oscillator circuit;
   a piezoelectric element having a temperature; and
   a protective device responsive to the temperature of the piezoelectric element, said protective device reducing power to the oscillator circuit as the temperature of the piezoelectric element increases and increasing power to the oscillator circuit as the temperature of the piezoelectric element decreases.

9. An apparatus as claimed in claim 8, wherein the protective device is an negative temperature coefficient thermistor.

10. An apparatus as claimed in claim 8, wherein a capacitor is connected in parallel with the protective device.

11. An apparatus as claimed in claim 8, wherein the apparatus further comprises an apparatus casing having component parts assembled together to define joints between the component parts, and at least one container carrying a liquid.

12. An apparatus as claimed in claim 8, wherein the piezoelectric element is supported by elastic means.

13. An apparatus as claimed in claim 12, wherein the elastic means is a spring.

14. An ultrasonic aerosol apparatus comprising:
   an oscillator circuit;
   a transistor connected in series with the oscillator circuit;
   a capacitor connected in parallel with the transistor;
   a piezoelectric element having a temperature; and a protective device responsive to the temperature of the piezoelectric element, said protective device reducing power to the oscillator circuit as the temperature of the piezoelectric element increases and increasing power to the oscillator circuit as the temperature of the piezoelectric element decreases.

15. An ultrasonic aerosol apparatus comprising:

an oscillator circuit;

a piezoelectric element having a temperature, the piezoelectric element being connected to a transistor via a capacitor, and a protective device responsive to the temperature of the piezoelectric element, said protective device reducing power to the oscillator circuit as the temperature of the piezoelectric element increases and increasing power to the oscillator circuit as the temperature of the piezoelectric element decreases.

16. An ultrasonic aerosol apparatus comprising:

an oscillator circuit;

a transistor connected in series with the oscillator circuit;

a capacitor connected in parallel with the transistor;

a piezoelectric element having a temperature, the piezoelectric element being connected to a collector of the transistor and to a base of the transistor via a capacitor, and a protective device responsive to the temperature of the piezoelectric element, said protective device reducing power to the oscillator circuit as the temperature of the piezoelectric element increases and increasing power to the oscillator circuit as the temperature of the piezoelectric element decreases.

17. An ultrasonic aerosol apparatus comprising:

an oscillator circuit;

a printed circuit board;

a piezoelectric element having a temperature and supported by elastic means, the elastic means electrically connecting the piezoelectric element and the printed circuit board; and a protective device responsive to the temperature of the piezoelectric element, said protective device reducing power to the oscillator circuit as the temperature of the piezoelectric element increases and increasing power to the oscillator circuit as the temperature of the piezoelectric element decreases.

* * * * *